(12) United States Patent
Schneider et al.

(10) Patent No.: US 10,948,278 B2
(45) Date of Patent: Mar. 16, 2021

(54) CALIBRATING A MAGNETIC SENSOR

(71) Applicant: Ascension Technology Corporation, Shelburne, VT (US)

(72) Inventors: Mark Robert Schneider, Willistown, VT (US); Charles Robertson, Shelburne, VT (US)

(73) Assignee: Ascension Technology Corporation, Shelburne, VT (US)

( * ) Notice: Subject to any disclaimer, the term of this patent is extended or adjusted under 35 U.S.C. 154(b) by 126 days.

(21) Appl. No.: 16/252,368

(22) Filed: Jan. 18, 2019

(65) Prior Publication Data

US 2019/0226826 A1 Jul. 25, 2019

Related U.S. Application Data

(60) Provisional application No. 62/619,232, filed on Jan. 19, 2018.

(51) Int. Cl.
*G01R 33/00* (2006.01)
*G01B 7/004* (2006.01)
(Continued)

(52) U.S. Cl.
CPC .............. *G01B 7/004* (2013.01); *G01C 17/38* (2013.01); *G01R 33/0035* (2013.01);
(Continued)

(58) Field of Classification Search
CPC .... G01B 7/004; G01C 17/38; G01R 33/0035; G06F 3/017; G06F 3/0346; G06F 3/012
See application file for complete search history.

(56) References Cited

U.S. PATENT DOCUMENTS

| 4,109,199 A | 8/1978 | Ball et al. |
| 6,242,907 B1 | 6/2001 | Clymer et al. |

(Continued)

FOREIGN PATENT DOCUMENTS

| EP | 2002290 | 1/2007 |
| EP | 2660561 | 1/2012 |

(Continued)

OTHER PUBLICATIONS

ES Search Report in ES Application No. 201930033, dated Jan. 30, 2020, 7 pages (with English translation).

(Continued)

*Primary Examiner* — Patrick Assouad
*Assistant Examiner* — Taqi R Nasir
(74) *Attorney, Agent, or Firm* — Fish & Richardson P.C.

(57) ABSTRACT

A calibration system comprising: a Helmholtz device comprising thee pairs of coils defining an inner volume, wherein each of the three pairs of coils is configured to generate a magnetic field that is uniform throughout the inner volume; a mount configured to accept a device that includes a magnetic sensor, wherein at least a portion of the mount is positioned within the inner volume such that the magnetic sensor is positioned at or near a center of the inner volume when the device is positioned on the mount; and a computer system configured to communicate with the Helmholtz device and the magnetic sensor, wherein the computer system is configured to: provide instructions to cause each of the three pairs of coils to generate a magnetic field; receive signals from the magnetic sensor that are based on characteristics of the magnetic fields received at the magnetic sensor; measure, based on the signals received from the magnetic sensor, one or more characteristics of the magnetic sensor; and determine, using a calibration algorithm, one or more calibration correction factors for the magnetic sensor (Continued)

based on the one or more characteristics of the magnetic sensor and the provided instructions.

23 Claims, 4 Drawing Sheets

(51) Int. Cl.
    *G06F 3/01*           (2006.01)
    *G01C 17/38*        (2006.01)
    *G06F 3/0346*      (2013.01)

(52) U.S. Cl.
    CPC .............. *G06F 3/012* (2013.01); *G06F 3/017* (2013.01); *G06F 3/0346* (2013.01)

(56) References Cited

U.S. PATENT DOCUMENTS

| | | |
|---|---|---|
| 6,252,393 B1 | 6/2001 | Hedengren |
| 6,335,617 B1 | 1/2002 | Osadchy et al. |
| 6,400,139 B1 | 6/2002 | Khalfin et al. |
| 6,427,079 B1 * | 7/2002 | Schneider ................ A61B 5/06 324/244 |
| 6,643,597 B1 | 11/2003 | Dunsmore |
| 7,719,261 B2 | 5/2010 | Geck et al. |
| 7,876,090 B2 | 1/2011 | Branson |
| 7,878,064 B2 | 2/2011 | Abbott et al. |
| 7,996,057 B2 | 8/2011 | Govari et al. |
| 8,635,043 B1 | 1/2014 | Olsson et al. |
| 9,316,714 B2 | 4/2016 | Rada et al. |
| 9,335,383 B2 | 5/2016 | Fukasawa et al. |
| 9,411,022 B2 | 8/2016 | Berman et al. |
| 9,559,793 B2 | 1/2017 | Meiyappan |
| 2006/0255795 A1 | 11/2006 | Higgins et al. |
| 2008/0262772 A1 | 10/2008 | Luinge |
| 2014/0188422 A1 | 7/2014 | Huber et al. |
| 2015/0145625 A1 | 5/2015 | Fukasawa et al. |
| 2015/0325151 A1 | 11/2015 | Tuchschmid et al. |
| 2016/0345286 A1 | 11/2016 | Jamieson |
| 2017/0067981 A1 | 3/2017 | Hannah et al. |
| 2017/0172409 A1 * | 6/2017 | Cavin .................... A61B 3/113 |
| 2017/0307891 A1 * | 10/2017 | Bucknor .................. G01S 1/70 |
| 2017/0351094 A1 | 12/2017 | Poulos et al. |
| 2018/0088185 A1 * | 3/2018 | Woods ................... G01R 35/00 |
| 2020/0182662 A1 | 6/2020 | Chave |

FOREIGN PATENT DOCUMENTS

| | | |
|---|---|---|
| WO | WO 2007/058526 | 5/2007 |
| WO | WO 2017/072407 A1 | 5/2017 |

OTHER PUBLICATIONS

DE Search Report in DE Application No. 102019200650, dated Sep. 6, 2019, 7 pages.

DE Search Report in DE Application No. 102019200652, dated Sep. 6, 2019, 7 pages.

ES Search Report in ES Application No. 201930033, dated Jul. 17, 2019, 5 pages.

ES Search Report in ES Application No. 201930034, dated Feb. 19, 2020, 7 pages (with English translation).

* cited by examiner

CALIBRATING A MAGNETIC SENSOR

CLAIM OF PRIORITY

This application claims priority under 35 USC § 119(e) to U.S. Patent Application Ser. No. 62/619,232, filed on Jan. 19, 2018, the entire contents of which are hereby incorporated by reference.

TECHNICAL FIELD

This disclosure relates to calibrating a magnetic sensor.

BACKGROUND

Electromagnetic Tracking (EMT) systems in general, and Augmented Reality (AR) and Virtual Reality (VR) systems in particular, can determine locations of devices in various contexts (e.g., gaming, medical, etc.). Such systems utilize a magnetic transmitter in proximity to a magnetic sensor such that the sensor and the transmitter can be spatially located relative to each other. Improper calibration of the transmitter with respect to the sensor (or vice versa) can cause the EMT system to report incorrect positions for the sensor or transmitter.

SUMMARY

Calibration of a magnetic sensor can be performed by positioning the sensor in a Helmholtz device (e.g., a Helmholtz coil) that is configured to generate one or more known magnetic fields (e.g., well-controlled and well-defined magnetic fields). In this way, the Helmholtz device acts as a virtual transmitter. The sensor, which may be incorporated into a device such as a head-mounted display (HMD), can be positioned in the Helmholtz device (e.g., near a center of a volume of the Helmholtz device), for example, a location at which the generated magnetic fields are known or expected to be known. In some implementations, the Helmholtz devices can generate the magnetic fields at a relative low frequency (e.g., 90 Hz) during calibration to minimize or eliminate interference in the generated magnetic fields that may otherwise be caused by materials of the HMD in which the sensor is incorporated.

The generated magnetic fields are received by the sensor and converted into one or more electrical signals indicative of one or more characteristics of the sensor (e.g., sensor characterization data).

The computer system can determine one or more calibration correction factors using a calibration algorithm. The calibration correction factors can be used to correct (e.g., calibrate) the sensor such that future readings obtained by the sensor result in accurate position and orientation determinations (e.g., relative to a coordinate system of the Helmholtz device, and relative to a transmitter used in an AR, VR, and/or EMT system).

In general, in an aspect, a calibration system includes a Helmholtz device that includes three pairs of coils defining an inner volume. Each of the three pairs of coils is configured to generate a magnetic field that is uniform throughout the inner volume. The calibration system also includes a mounting surface (e.g., a mount) configured to accept a device that includes a magnetic sensor. At least a portion of the mount is positioned within the inner volume such that the magnetic sensor is positioned at or near a center of the inner volume when the device is positioned on the mount. The calibration system also includes a computer system configured to communicate with the Helmholtz device and the magnetic sensor. The computer system is configured to provide instructions to cause each of the three pairs of coils to generate a magnetic field, receive signals from the magnetic sensor that are based on characteristics of the magnetic fields received at the magnetic sensor, measure, based on the signals received from the magnetic sensor, one or more characteristics of the magnetic sensor, and determine, using a calibration algorithm, one or more calibration correction factors for the magnetic sensor based on the one or more characteristics of the magnetic sensor and the provided instructions.

Implementations can include one or more of the following features.

In some implementations, the computer system is configured to create a calibration file that includes the calibration correction factors, and apply the calibration file to the magnetic sensor.

In some implementations, the device is a head-mounted display, and the mount is configured to hold the head-mounted display and the magnetic sensor in a fixed position and orientation relative to the Helmholtz device.

In some implementations, the device is configured to communicate with one or both of the computer system or the Helmholtz device.

In some implementations, the device is configured for use in one of both of an Augmented Reality (AR) system or a Virtual Reality (VR) system.

In some implementations, each of the three pairs of coils is configured to generate the magnetic field at a frequency of less than 100 Hz.

In some implementations, each of the three pairs of coils is configured to generate the magnetic field at a frequency of 90 Hz.

In some implementations, the magnetic sensor is configured to receive magnetics fields having frequencies of more than 30 KHz when in use in an AR system or a VR system In some implementations, the mount is configured to accept a calibrated magnetic sensor. The computer system is configured to provide instructions to cause each of the three pairs of coils to generate a second magnetic field that is uniform throughout the inner volume, receive signals from the calibrated magnetic sensor that are based on characteristics of the second magnetic fields received at the calibrated magnetic sensor, measure, based on the signals received from the calibrated magnetic sensor, one or more characteristics of the calibrated magnetic sensor, and determine, using a calibration algorithm, one or more calibration correction factors for one or more of the three pairs of coils based on the one or more characteristics of the calibrated magnetic sensor.

In some implementations, the computer system is configured to create one or more calibration files that include the calibration correction factors, and apply the one or more calibration files to the one or more of the three pairs of coils.

In some implementations, the instructions for causing each of the three pairs of coils to generate the magnetic field are adjusted based on the one or more calibration correction factors for one of more of the three pairs of coils.

In general, in another aspect, a method includes providing, by a computer system, instructions to cause current to flow through each of three pairs of coils that define an inner volume. The current causes each of the three pairs of coils to generate a magnetic field that is uniform throughout the inner volume. The method also includes receiving, from a magnetic sensor incorporated into a device that is positioned within the inner volume, signals that are based on characteristics of the magnetic fields received at the magnetic sensor. The method also includes measuring, based on the signals received from the magnetic sensor, one or more characteristics of the magnetic sensor. The method also includes determining, using a calibration algorithm, one or more calibration correction factors for the magnetic sensor based on the one or more characteristics of the magnetic sensor and the provided instructions.

Implementations can include one or more of the following features.

In some implementations, the method also includes creating a calibration file that includes the calibration correction factors, and applying the calibration file to the magnetic sensor.

In some implementations, the device is a head-mounted display, and a mount is configured to hold the head-mounted display and the magnetic sensor in a fixed position and orientation relative to the three pairs of coils.

In some implementations, one or more of the magnetic sensor, the device, or the three pairs of coils are configured to communicate with the computer system.

In some implementations, the device is configured for use in one of both of an Augmented Reality (AR) system or a Virtual Reality (VR) system.

In some implementations, each of the three pairs of coils is configured to generate the magnetic field at a frequency of less than 100 Hz.

In some implementations, each of the three pairs of coils is configured to generate the magnetic field at a frequency of 90 Hz.

In some implementations, the magnetic sensor is configured to receive magnetics fields having frequencies of more than 30 KHz when in use in an AR system or a VR system In some implementations, the method includes providing, by a computer system, instructions to cause second current to flow through each of the three pairs of coils. The second current causes each of the three pairs of coils to generate a second magnetic field that is uniform throughout the inner volume. The method also includes receiving, from a calibrated magnetic sensor that is positioned within the inner volume, signals that are based on characteristics of the second magnetic fields received at the calibrated magnetic sensor. The method also includes measuring, based on the signals received from the calibrated magnetic sensor, one or more characteristics of the calibrated magnetic sensor. The method also includes determining, using a calibration algorithm, one or more calibration correction factors for one or more of the three pairs of coils based on the one or more characteristics of the calibrated magnetic sensor.

In some implementations, the method also includes creating one or more calibration files that include the calibration correction factors, and applying the one or more calibration files to the one or more of the three pairs of coils.

In some implementations, the instructions for causing each of the three pairs of coils to generate the magnetic field are adjusted based on the one or more calibration correction factors for one of more of the three pairs of coils.

Advantages of the system described herein include using a dedicated calibration device to calibrate multiple sensors (e.g., multiple devices under test (DUT)) quickly and accurately. The Helmholtz device does not require moving parts (e.g. moving a transmitter to multiple different locations). Rather, the Helmholtz device acts as a virtual transmitter that generates one or more magnetics fields that cause the sensor to provide particular characterization data. The Helmholtz device simplifies the calibration procedure and speeds up calibration and testing. The need for a three-axis translation system (e.g., such as one that includes a gantry) is eliminated.

Further, the sensor can be calibrated while it is incorporated into a device (e.g., a HMD), thereby eliminating the need to remove the sensor from the HMD prior to calibration. The resulting calibration can have improved accuracy due to the calibration being performed on the device (e.g., the HMD) in which the sensor is ultimately used (e.g., when implemented in an AR, VR, and/or EMT system). In some implementations, the paired coils of the Helmholtz device are configured to generate magnetic fields at a relatively low frequency (e.g., 90 Hz) to minimize interference that may otherwise be caused by materials of the HMD. For example, the HMD in which the sensor is incorporated may include one or more materials (e.g., metal materials) that may cause eddy currents to be produced in response to magnetic fields having relatively high frequencies (e.g., 34 KHz). Such eddy currents may cause the generated magnetic fields to be distorted, such that the sensor receives distorted magnetic fields. However, magnetic fields generated at a relatively low frequency of about 90 Hz can reduce or eliminate the occurrence of eddy currents, thereby allowing the sensor to receive the intended (e.g., true) magnetic fields generated by the Helmholtz device.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system can be used in gaming and/or surgical settings to track devices (e.g., gaming controllers, head-mounted displays, medical equipment, robotic arms, etc.), thereby allowing their respective three-dimensional positions and orientations to be known to a user of the system. Augmented Reality (AR) and Virtual Reality (VR) systems also use EMT systems to perform head, hand, and body tracking, for example, to synchronize the user's movement with the AR/VR content. Such systems use a magnetic transmitter in proximity to a magnetic sensor to determine the position and/or orientation of the sensor relative to the transmitter. Transmitters and sensors used in such systems are calibrated to ensure that the transmitters and sensors can provide accurate position and orientation information to the user. If the sensor or transmitter is not calibrated or is improperly calibrated, accuracy can be greatly diminished.

Calibration of a magnetic sensor can be performed by a calibration system that includes a Helmholtz device (e.g., a Helmholtz coil). The sensor can be positioned in the Helmholtz device, which is configured to generate one or more uniform magnetic fields (well-controlled and well-defined magnetic fields). In this way, the Helmholtz device acts as a virtual transmitter. For example, a mounting surface (e.g., a mount) positioned in the Helmholtz device is configured to receive a device (e.g., a head-mounted display (HMD)) that includes the sensor. The device and the sensor are positioned at a particular location (e.g., a central location) of the Helmholtz device at which the magnetic fields are uniform. A computer system in communication with the Helmholtz device can provide instructions to cause the Helmholtz device to generate one or more magnetic fields (e.g., well-controlled and well-defined magnetic fields). For example, the particular instructions may cause the Helmholtz device to generate one or more magnetic fields that are expected to have particular characteristics. In this way, characteristics of the generated magnetic fields are known for the location at which the device and sensor are positioned (e.g., assuming the Helmholtz device is calibrated). In some implementations, the Helmholtz device may be calibrated prior to calibration of the sensor, as described in more detail below.

The sensor receives (e.g., senses) the generated magnetic fields and converts the magnetic fields into one or more electrical signals indicative of one or more characteristics of the sensor (e.g., sensor characterization data). In some examples, the sensor characterization data may be indicative of the position and orientation of the sensor relative to the Helmholtz device.

Based on the characteristics of the magnetic sensor and the provided instructions for causing the Helmholtz device to generate the one or more magnetic fields, the computer system can determine one or more calibration correction factors according to a calibration algorithm. The calibration correction factors can be used to calibrate the sensor such that future readings obtained by the sensor result in accurate P&O data determined by the computer system, and accurate P&O data determined by an AR, VR, and/or EMT system in which the sensor is included.

Figure 1:
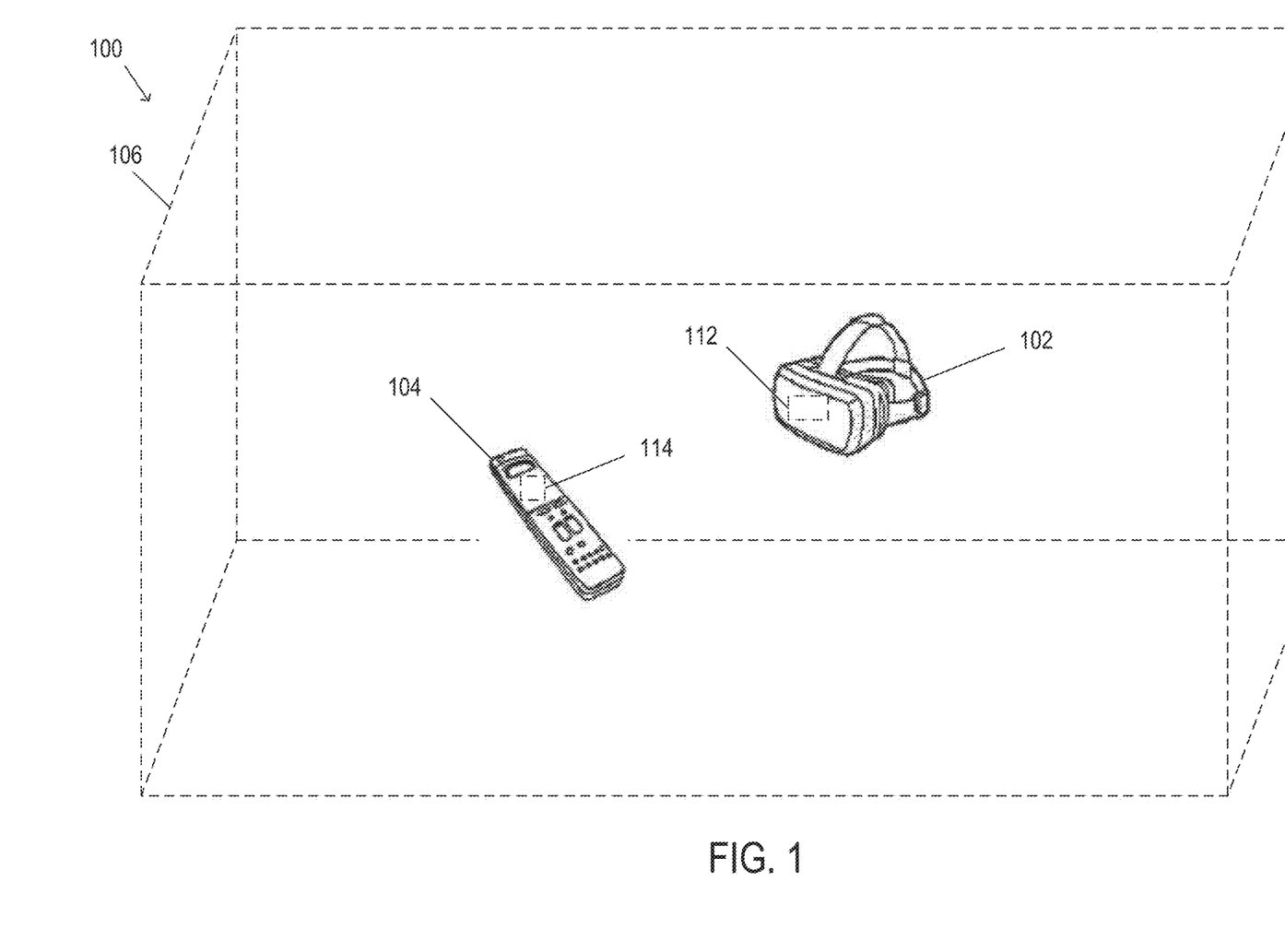
FIG. 1 is a schematic diagram of an example Electromagnetic Tracking (EMT) system.

FIG. 1 shows an example of an EMT system 100 that can be used as part of a VR/AR system. The EMT system 100 includes at least a head-mounted display (HMD) 102 that includes a magnetic sensor 112 and a controller 104 that includes a magnetic transmitter 114. The HMD 102 and the controller 104 are configured to track position (e.g., in x, y, and z) and orientation (e.g., in azimuth, altitude, and roll) in three-dimensional space relative to each other. For example, the HMD 102 is configured to track the sensor 112 of HMD 102 relative to a reference frame defined by transmitter 114 of controller 104. In some implementations, the transmitter 114 of the controller 104 is configured to track the sensor 112 of the HMD 102 relative to a reference frame defined by the position and orientation of the transmitter 114, and/or the sensor 112 of the HMD 102 is configured to track the transmitter 114 of the controller 104 relative to a reference frame defined by the position and orientation of the sensor 112. The particular sensor 112 and transmitter 114 employed by the EMT system 100 may be determined by the procedure type, measurement performance requirements, etc.

The position and orientation of the HMD 102 and the controller 104 can be tracked relative to each other within a tracking volume 106. While the tracking volume 106 is illustrated as being a defined space, it should be understood that the tracking volume 106 may be any three-dimensional space, including dimensionless three-dimensional spaces (e.g., large indoor and/or outdoor areas, etc.).

In some implementations, the transmitter 114 includes three orthogonally wound magnetic coils, referred to herein as the x, y, and z coils. Electrical currents traveling through the three coils cause the coils to produce three magnetic fields (e.g., orthogonal sinusoidal magnetic fields) at three frequencies (e.g., three different frequencies). The three frequencies may be three closely spaced frequencies, e.g., 34 KHz, 34.25 KHz, and 34.5 KHz, although other frequencies can also or alternatively be used. In some implementations, the coils may produce magnetic fields at the same frequency (e.g., 34 KHz). The sensor 112 also includes three wound (e.g., orthogonally wound) magnetic coils, referred to herein as the x, y, and z coils. Voltages are induced in the coils of the sensor 112 in response to the sensed magnetic fields by means of magnetic induction. Each coil of the sensor 112 generates an electrical signal for each of the magnetic fields generated by the coils of the transmitter 114; for example, the x coil of the sensor 112 generates a first electrical signal in response to the magnetic field generated by (and, e.g., sensed by/received from) the x coil of the transmitter 114, a second electrical signal in response to the magnetic field generated by (and, e.g., sensed by/received from) the y coil of the transmitter 114, and a third electrical signal in response to the magnetic field generated by (and, e.g., sensed by/received from) the z coil of the transmitter 114. The y and z coils of the sensor 112 similarly generate electrical signals for each of the magnetic fields generated by the coils of the transmitter 114.

In the illustrated example, the sensor 112 is incorporated into the EMT system 100, and as such, the data from the sensor 112 is indicative of the position and orientation of the sensor 112 relative to the transmitter 114, or vice versa. The data from the sensor 112 can be represented as a matrix of data (e.g., a 3×3 matrix), which can be resolved into the position and orientation of the sensor 112 with respect to the transmitter 114, or vice versa. In this way, the position and orientation of the sensor 112 and the transmitter 114 is measured. In particular, electronics incorporated into the HMD 102 are configured to determine the position and orientation of the controller 104 relative to the HMD 102 based on the characteristics of the magnetic fields generated by the transmitter 114 and the various electrical signals generated by the sensor 112. As described below, a separate computer system (e.g., the computer system 212 of FIGS. 2 and 3) may be configured to determine the position and orientation of a sensor and/or a transmitter.

If the transmitter 114 and/or the sensor 112 is not calibrated accurately, the determined (e.g., measured) position and orientation of the transmitter 114 and/or sensor 112 may not reflect the true (e.g., actual) position and orientation. As such, before the sensor 112 (e.g., incorporated into the HMD 102) is used in the EMT system 100, the sensor 112 should be calibrated.

Calibrating the Sensor

Figure 2:
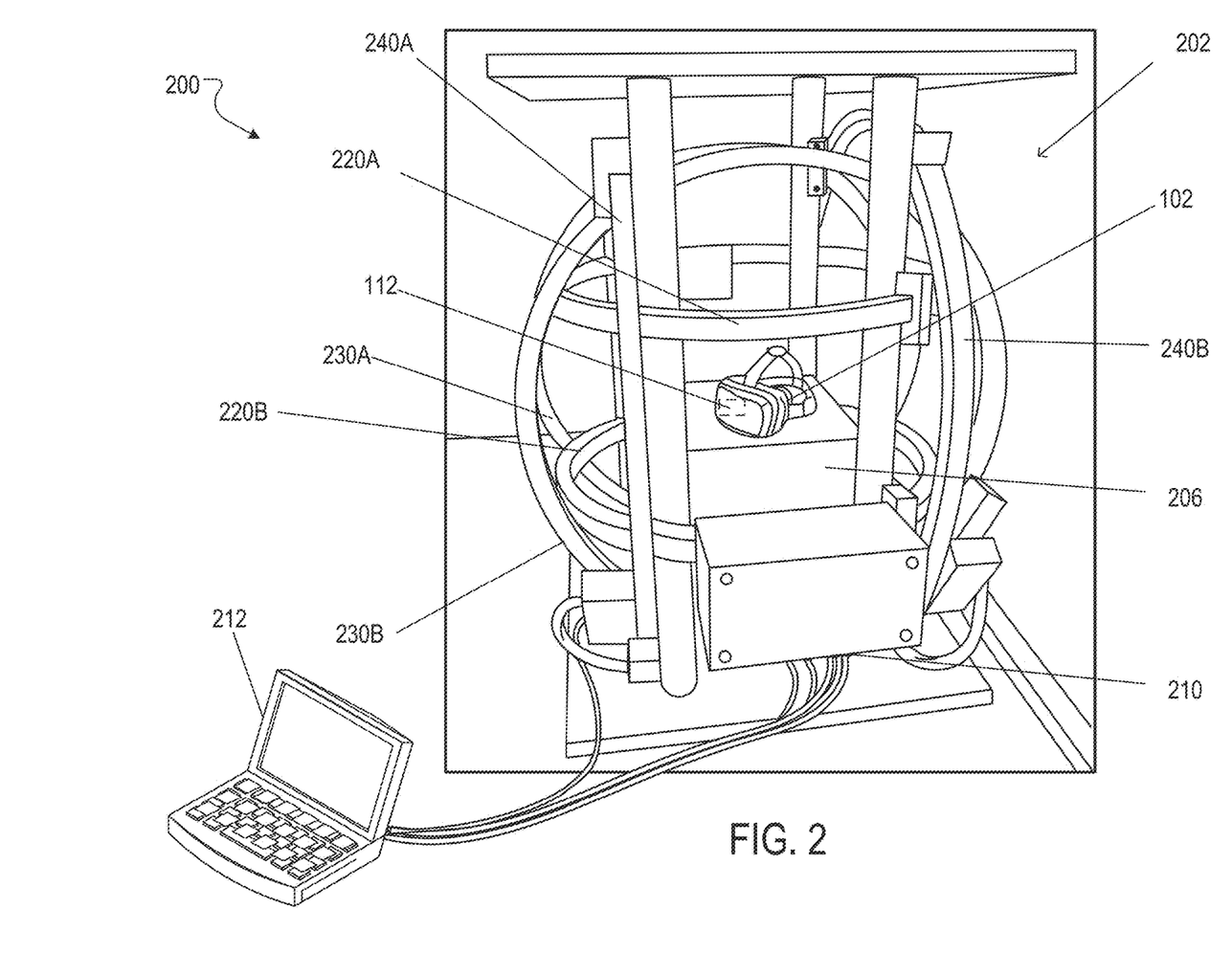
FIG. 2 shows an example of a calibration system that includes Helmholtz device for assisting in calibrating a sensor for use in the EMT system of FIG. 1.

FIG. 2 shows an example of a calibration system 200 that includes a Helmholtz device 202 (e.g., a Helmholtz coil) for calibrating a sensor (e.g., the sensor 112 of FIG. 1). The Helmholtz device 202 may be used to calibrate the sensor 112 while the sensor 112 is incorporated in (e.g., housed in) the HMD 102. The Helmholtz device 202 may be configured to calibrate a plurality of devices under test (e.g., DUT). That is, the Helmholtz device 202 can calibrate a first DUT in the form of a first sensor incorporated in a first HMD, a second DUT in the form of a second sensor incorporated in a second HMD, etc. Such calibration of multiple DUT can ensure that all sensors 112 and HMDs 102 across various EMT systems 100 have common calibration characteristics.

The Helmholtz device 202 includes three sets of paired coils 220A, 220B, 230A, 230B, 240A, 240B, that can be arranged and grouped together to create uniform magnetic fields along a coordinate system defined by the Helmholtz device 202 (e.g., x, y, and z axes). The uniformity of the magnetic fields depends on the size, shape, and geometry of the paired coils, with larger coils typically providing larger central regions of uniformity. Such a Helmholtz device 202 is advantageously used in calibration of the sensor 112 because the magnetic fields throughout an inner volume of the Helmholtz device 202 (e.g., where the sensor 112 and HMD 102 are positioned) is uniform, well known, and well defined. The magnetic fields throughout the inner volume of the Helmholtz device 202 (e.g., bounded and defined by the paired coils 220, 230, 240) are kept constant as the magnetic fields form the basis for the calibration of the sensor 112. The calibration system 200 includes a mounting surface. In particular, in the illustrated example, the calibration system 200 includes a mount 206, at least a portion of which resides within the inner volume of the Helmholtz device 202 defined by the paired coils 220, 230, 240. The mount 206 is configured to accept a device for calibration. For example, the HMD 102 including the sensor 112 of FIG. 1 can be placed on the mount 206 for calibration. In some implementations, the mount 206 is positioned such that the sensor 112 is positioned at or near the center of the volume of the Helmholtz device 202 when the HMD 102 is positioned on the mount 206. In some implementations, the mount 206 includes one or more mechanisms (e.g., pegs or pins) configured to interface with corresponding apertures of the HMD 102 to assist in holding the HMD 102 in position on the mount 206 during calibration. In some implementations, the mount 206 may alternatively or additionally include additional fixing elements, such as a harness, for assisting in holding the HMD 102 in place.

The calibration system 200 also includes a communications interface 210 that allows the Helmholtz device 202 to interact with a computing device, such as a computer system 212. That is, the communications interface 210 facilitates communication between the Helmholtz device 202 and the computer system 212. In some implementations, the computer system 212 is part of the calibration system 200. While the computer system 212 is illustrated as being connected to the Helmholtz device 202 by a wired connection, in some implementations, the Helmholtz device 202 may include wireless communication capabilities such that the Helmholtz device 202 can wirelessly communicate with the computer system 212. The paired coils 220, 230, 240 are connected to the communications interface 210 such that the computer system 212 can communicate with the paired coils 220, 230, 240 (e.g., provide signals and/or instructions to the paired coils 220, 230, 240).

The HMD 102 and the sensor 112 are positioned on the mount 206 such that the sensor 112 is in a fixed position and orientation within the uniform fields of the Helmholtz device 202. The computer system 212 is configured to provide instructions to cause the Helmholtz device 202 to generate the one or more magnetic fields (e.g., well-controlled, well-defined, uniform magnetic fields). For example, the computer system 212 can provide instructions that include electrical parameters (e.g., current parameters, voltage parameters, etc.) that cause the paired coils 220, 230, 240 to generate the magnetic fields.

In some implementations, rather than and/or in addition to the computer system 212 being provided as a separate component of the calibration system 200, the Helmholtz device 202 may include one or more computer components such that the Helmholtz device 202 itself includes and/or acts as a computer system. For example, the Helmholtz device 202 may include computer components that cause the Helmholtz device 202 to perform various functionality as described herein with respect to the computer system 212 (e.g., generating the magnetic fields, etc.).

Before the sensor 112 is calibrated, the Helmholtz device 202 may undergo its own calibration to ensure that the paired coils 220, 230, 240 are calibrated. For example, the Helmholtz device 202 may be calibrated to ensure that the instructions provided to the Helmholtz device 202 to cause the paired coils 220, 230, 240 to generate the magnetic fields do in fact result in the paired coils 220, 230, 240 generating magnetic fields having expected characteristics. Such calibration of the Helmholtz device 202 is described in more detail below.

A first DUT is placed on the mount 206 (e.g., after calibrating the Helmholtz device 202 or after confirming that the Helmholtz device 202 is calibrated). In particular, the HMD 102 including the sensor 112 is positioned on the mount 206. In some implementations, the mount 206 may include electrical contacts that are configured to form electrical connections with electrical contacts of the HMD 102 such that the Helmholtz device 202 and the HMD 102 (e.g., and the sensor 112) can interact and exchange information. In some implementations, the HMD 102 may otherwise be electrically connected to the Helmholtz device 202 and/or connected to the computer system 212 (e.g., by a universal serial bus (USB) cable). In some implementations, the HMD 102 may be configured to exchange information with the Helmholtz device 202 and/or the computer system 212 over a wireless connection.

With the HMD 102 in place on the mount 206, the computer system 212 can cause the paired coils 220, 230, 240 to generate the one or more uniform magnetic fields. In particular, the computer system 212 provides instructions to cause current to flow through a first pair of the coils 220 (e.g., the x coils) to cause an x magnetic field to be generated, current to flow through a second pair of the coils 230 (e.g., the y coils) to cause a y magnetic field to be generated, and current to flow through a third pair of the coils 240 (e.g., the z coils) to cause a z magnetic field to be generated, thereby causing the Helmholtz device 202 to produce three orthogonal magnetic fields. These may be sinusoidal, pulsed DC, or some other excitation. The x, y, and z fields may be generated at particular frequencies (e.g., the same frequency, different frequencies, etc.) or be time multiplexed.

The magnetic fields generated by the Helmholtz device 202 are received at the sensor 112 and induce voltages in the x, y, and z coils of the sensor 112. The voltages are induced in the coils of the sensor 112 in response to the sensed magnetic fields by means of magnetic induction. Each coil of the sensor 112 generates an electrical signal for each of the magnetic fields generated by the Helmholtz device 202. For example, the x coil of the sensor 112 generates a first electrical signal in response to the magnetic field received from the x coils 220, a second electrical signal in response to the magnetic field received from the y coils 230, and a third electrical signal in response to the magnetic field received from the z coils 240. The y and z coils of the sensor 112 similarly generate electrical signals for each of the magnetic fields received from each of the x 220, y 230, and z 240 coils.

One or more characteristics of the magnetic sensor (e.g., sensor characterization data) are measured based on the signals received from the sensor 112. In some implementations, the data from the sensor 112 can be represented as a matrix of characterization data (e.g., a 3×3 matrix).

One or more calibration correction factors are determined for the sensor 112 based on the one or more characteristics of the sensor 112 and the provided instructions for causing the Helmholtz device 202 to generate the magnetic fields. The calibration correction factors can be applied to the sensor 112 to correct inaccuracies and/or to minimize errors due to DUT unit-to-unit variations (e.g., between various sensors incorporated across various systems). The calibration correction factors are determined using a calibration algorithm. In some implementations (e.g., implementations in which the Helmholtz device 202 is not calibrated), the calibration correction factors for the sensor 112 are determined based in part on calibration correction factors for the Helmholtz device 202, as described in more detail below with respect to FIG. 3. In some implementations, the calibration correction factors may be stored on the sensor 112, stored on electronics of the HMD 102, or stored elsewhere in the EMT system 100 in which the sensor 112 is ultimately incorporated. In some implementations, calibration correction factors may be stored in network storage (e.g., on a server, such as a cloud server) for later use to calibrate the DUT. In some implementations, calibration of the sensor 112 may take approximately one minute or less.

In some implementations, it may be determined that the sensor 112 does not require calibration. As such, the calibration correction factors may be determined to be zero. In other words, the EMT system 100 may determine that the sensor 112 provides relatively accurate data and that calibration of the sensor 112 is not required, and such may be indicated by calibration correction factors with a value of zero being determined. If calibration of the sensor 112 is not required, the sensor 112 may be left as-is (e.g., no calibration correction factors are applied to the sensor 112, or calibration correction factors having a value of zero are applied to the sensor 112, thereby resulting in no change to the way that the sensor 112 generates and provides data).

As described above, the sensor 112 is calibrated while the sensor 112 is incorporated in (e.g., inside) a housing of the HMD 102. In some implementations, the materials of the housing of the HMD 102 may cause distortions in the magnetic fields generated by the Helmholtz device 202. For example, eddy current produced in metal materials of HMD 102 may cause the magnetic fields to be distorted at or near the HMD 102. As a result, the magnetic fields that are received at the sensor 112 are different from the magnetic fields that are expected to be received at the sensor 112 (e.g., expected according to the instructions provided by the computer system 212). Because the magnetic fields actually received by the sensor 112 may be different from those expected to be received, the electrical signals indicative of the characteristics of the sensor 112 are based on the distorted magnetic fields, and the calibration data computed by the computer system 212 may be inaccurate. This may cause inaccurate P&O data to be calculated.

In some implementations, potential distortions in the generated magnetic fields can be minimized or eliminated by controlling the frequencies at which the paired coils 220, 230, 240 generate the magnetic fields. Eddy current excitations of components in HMD 102 can be minimized by reducing the frequency of magnetic fields. For example, computer system 212 may cause the paired coils 220, 230, 240 to run at a particular frequency, such as a relative low frequency. In some implementations, the paired coils 220, 230, 240 may run at a frequency of less than 100 Hz (e.g., 90 Hz), although other frequencies may alternatively be used depending on the circumstances. Measurements at these lower frequencies can then be adjusted to provide sensor characteristics at higher operating frequencies. In other words, the measured one or more characteristics of the sensor 112 may be adjusted based on an operating frequency to be used in a system in which the sensor 112 is later incorporated. In some implementations, the particular frequency at which the paired coils 220, 230, 240 run is chosen based on particular characteristics of the HMD 102. As described above, the transmitter 114 of the EMT system 100 may be configured to run at frequencies in the order of about 30 KHz or more (e.g., 34 KHz). Thus, the frequency at which the sensor 112 is calibrated (e.g., 90 Hz) may be different than the frequency of the magnetic fields (e.g., 34 KHz) received by the sensor 112 in a use case (e.g., an actual implementation of the EMT system 100). That is, the frequency at which the sensor 112 is calibrated may be different than the frequency at which the sensor 112 operates in an EMT, AR, and/or VR system implementation.

Calibrating the Helmholtz Device

As described above, the Helmholtz device 202 may undergo a calibration process such that the fields generated by the paired coils 220, 230, 240 are known in amplitude and geometry. One or more calibration correction factors (e.g., Helmholtz calibration correction factors, generally referred to as Helmholtz calibration data) can then be used to algorithmically mimic an ideal (e.g., perfect) Helmholtz device. In this way, the calibration correction factors can be used to adjust the instructions provided by the computer system 212 to ensure that the magnetic fields generated by the paired coils 220, 230, 240 have expected characteristics. A sensor that is known to be calibrated using other means (e.g., known to produce accurate results/characterization data when used with this calibration) can be used to perform such a calibration of the Helmholtz device 202.

Figure 3:
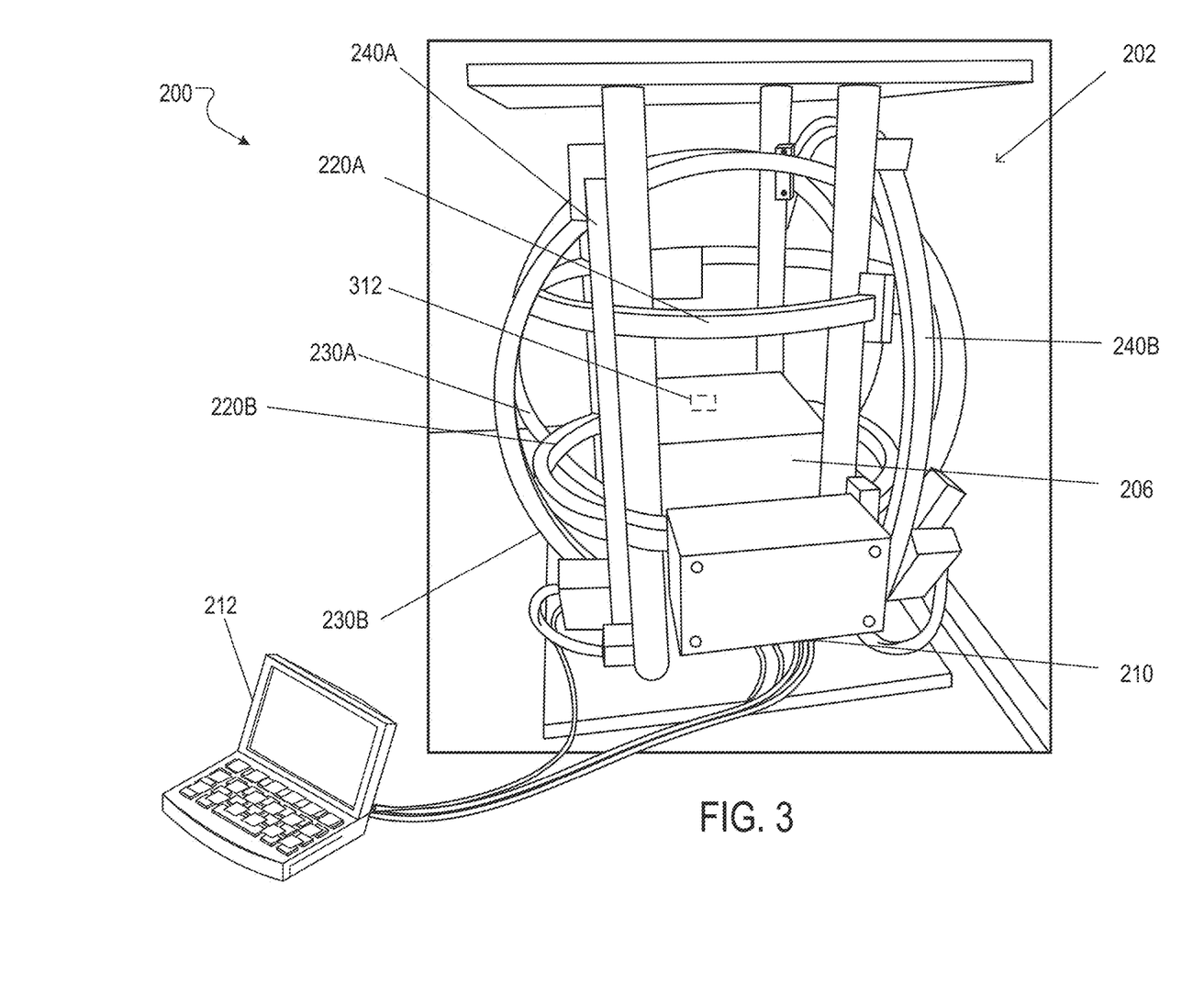
FIG. 3 shows the calibration system and Helmholtz device of FIG. 2 operating in a self-calibration mode.

FIG. 3 shows an example of the Helmholtz device 202 of FIG. 2 operating in a self-calibration mode. In this example, the HMD 102 has been replaced with a reference device, such as a reference sensor 312 (e.g., a calibrated sensor) that is known to produce accurate results when used with its calibration. In other words, the calibrated reference sensor 312 is known to generate electrical signals in response to sensing the generated magnetic fields that result in the computer system 212 providing accurate characterization data, provided that the paired coils 220, 230, 240 are calibrated.

The reference sensor 312 is positioned in the mount 206 such that the reference sensor 312 assumes a fixed position at or near the center of the volume of the Helmholtz device 202. In some implementations, the reference sensor 312 is electrically connected to the Helmholtz device 202 via one or more electrical contacts in the mount 206 or via a separate wired electrical connection. In some implementations, the reference sensor 312 is connected to the computer system 212 by a wireless or wires connection (e.g., via a USB cable). In some implementations, the reference sensor 312 may be configured to exchange information with the Helmholtz device 202 and/or the computer system 212 over a wireless connection.

With the reference sensor 312 in place on the mount 206, the computer system 212 can cause the paired coils 220, 230, 240 to generate one or more uniform magnetic fields. In particular, the computer system 212 provides instructions to cause current to flow through each of the paired coils 220, 230, 240, which causes the paired coils 220, 230, 240 to produce three orthogonal sinusoidal magnetic fields at particular frequencies. The magnetic fields generated by the paired coils 220, 230, 240 are received at the reference sensor 312 and cause voltages to be induced in the coils of the reference sensor 312.

One or more characteristics of the reference sensor 312 (e.g., reference sensor characterization data) are measured based on the signals received from the reference sensor 312. In some implementations, the data from the reference sensor 312 can be represented as a matrix of characterization data (e.g., a 3×3 matrix). Because the reference sensor 312 is known to be calibrated (e.g., by other means), the reference sensor characterization data is known to represent ideal characteristics of a sensor assuming a calibrated Helmholtz device is provided. Therefore, any inaccuracies in the reference sensor characterization data can be attributed to inaccuracies in the Helmholtz device 202. Therefore, the reference sensor characterization data can be used to determine calibration data for the Helmholtz device 202.

One or more calibration correction factors are determined for the Helmholtz device 202 based on the one or more characteristics of the reference sensor 312 and according to a calibration algorithm. The calibration correction factors for the Helmholtz device 202 are sometimes referred to as Helmholtz calibration data. In some implementations, the Helmholtz calibration data is represented as a matrix of data (e.g., a 3×3 matrix). The Helmholtz calibration data can be used to adjust the instructions provided by the computer system 212 for causing the transmitter coils to generate the magnetic fields. As such, the magnetic fields generated during calibration of the sensor 112 have known characteristics (e.g., known amplitude and geometry). In this way, the sensor 112 is calibrated by a calibrated Helmholtz device 202 that is confirmed to generate uniform, well-controlled, and well-defined magnetic fields. In other words, the Helmholtz calibration data is used to adjust the Helmholtz device 202 into an ideal (e.g., perfect) Helmholtz device. In some implementations, the Helmholtz device 202 may be calibrated according to the techniques described herein before DUTs are calibrated.

The calibration correction factors for the Helmholtz device 202 may be determined for one or more of the paired coils 220, 230, 240. In some implementations, each of the paired coils 220, 230, 240 of the Helmholtz device 202 may be independently calibrated. For example, zero, one, two, or three of the pairs of coils 220, 230, 240 may be calibrated. In some implementations, only one of each pair of coil may be determined to require calibration.

In some examples, the one or more calibration correction factors for the Helmholtz device 202 may be applied to the paired coils 220, 230, 240 to correct inaccuracies and/or to minimize errors may otherwise occur during future calibration of a DUT sensor 112. In some implementations, the calibration correction factors may be stored on electronics of the Helmholtz device 202. In some implementations, calibration correction factors may be stored in network storage (e.g., on a server, such as a cloud server) for later use to calibrate one or more of the paired coils 220, 230, 240. In some implementations, calibration of the Helmholtz device 202 (e.g., calibration of one or more of the paired coils 220, 230, 240) may take approximately one minute or less.

Once the Helmholtz device 202 (e.g., the paired coils 220, 230, 240) has been calibrated, the Helmholtz device 202 may be used for calibration of various DUT sensors 112.

Operating the Calibration Device

Whether the Helmholtz device 202 is being used to calibrate a DUT or being calibrated itself, a user of the Helmholtz device 202 and the computer system 212 can perform the calibration procedure by interacting with the computer system 212. In some implementations, the computer system 212 is configured to provide instructions for the user via a graphical user interface (GUI). For example, the computer system 212 may be a laptop computer that is configured to execute a program used for calibrating a DUT or calibrating the Helmholtz device 202. The program can cause a screen of the laptop to display instructions to assist the user in carrying out the particular calibration procedure. For example, the instructions can include textual, visual, and/or audible instructions instructing the user to place the HMD 102 or the reference sensor 312 on the mount 206, electrically connect the HMD 102 or the reference sensor 312 to the mount 206 or computer system 212 (e.g., if required to form a wired connection), connect the computer system 212 to the Helmholtz device 202 (e.g., if required to form a wired connection), etc.

In some implementations, the program operating on the computer system 212 may include one or more user-selectable values and/or user-input fields for allowing the user to define one or more characteristics of the calibration procedure. For example, the program may allow the user to specify particular frequencies at which the paired coils 220, 230, 240 are to operate in order to generate respective magnetic fields. In some implementations, the program may allow the user to store, recall, and/or apply calibration correction values to the sensor 112 (e.g., during calibration of the sensor 112) and/or to one or more of the paired coils 220, 230, 240 (e.g., during calibration of the Helmholtz device 202). In some implementations, the program is configured to provide an indication that the sensor 112 requires calibration, an indication that the sensor 112 does not require calibration, an indication that the Helmholtz device 202 requires calibration, and/or an indication that the Helmholtz device 202 does not require calibration (e.g., a pass/fail result). For examples in which calibration is required, the program may provide a user interface element that can allow the user to initiate a calibration procedure upon interaction with the user interface element.

In some implementations, the Helmholtz device 202 and the computer system 212 may be configured to perform calibrations on different types (e.g., different models) of sensors and/or HMDs. In some implementations, the program may accept an input indicative of the model of the sensor and/or HMD to be calibrated. Particular parameters stored on the computer system 212 may be implemented during the calibration based on the model of the sensor and/or HMD in use. For example, a first model of sensor may call for particular magnitudes of currents to pass through the paired coils 220, 230, 240 of the Helmholtz device 202, and/or certain frequencies for the magnetic fields to be generated by the paired coils 220, 230, 240, and a second model of sensor may call for different magnitudes of currents to pass through the paired coils 220, 230, 240 of the Helmholtz device 202, and/or different frequencies for the magnetic fields to be generated by the paired coils 220, 230, 240.

In some implementations, the calibration correction factors for a particular DUT sensor 112 or for one or more of the paired coils 220, 230, 240 may be included as part of a calibration file that is created by the program operating on the computer system 212. For example, once the one or more calibration correction factors are determined, a calibration file may be created that can be used to update a particular DUT sensor 112 or a particular one or more of the paired coils 220, 230, 240. In some implementations, the calibration file may be "flashed" to the DUT sensor 112 or the paired coil 220, 230, 240. In some implementations, a firmware of the DUT sensor 112 and/or the paired coil 220, 230, 240 can be updated based on the calibration file.

Figure 4:
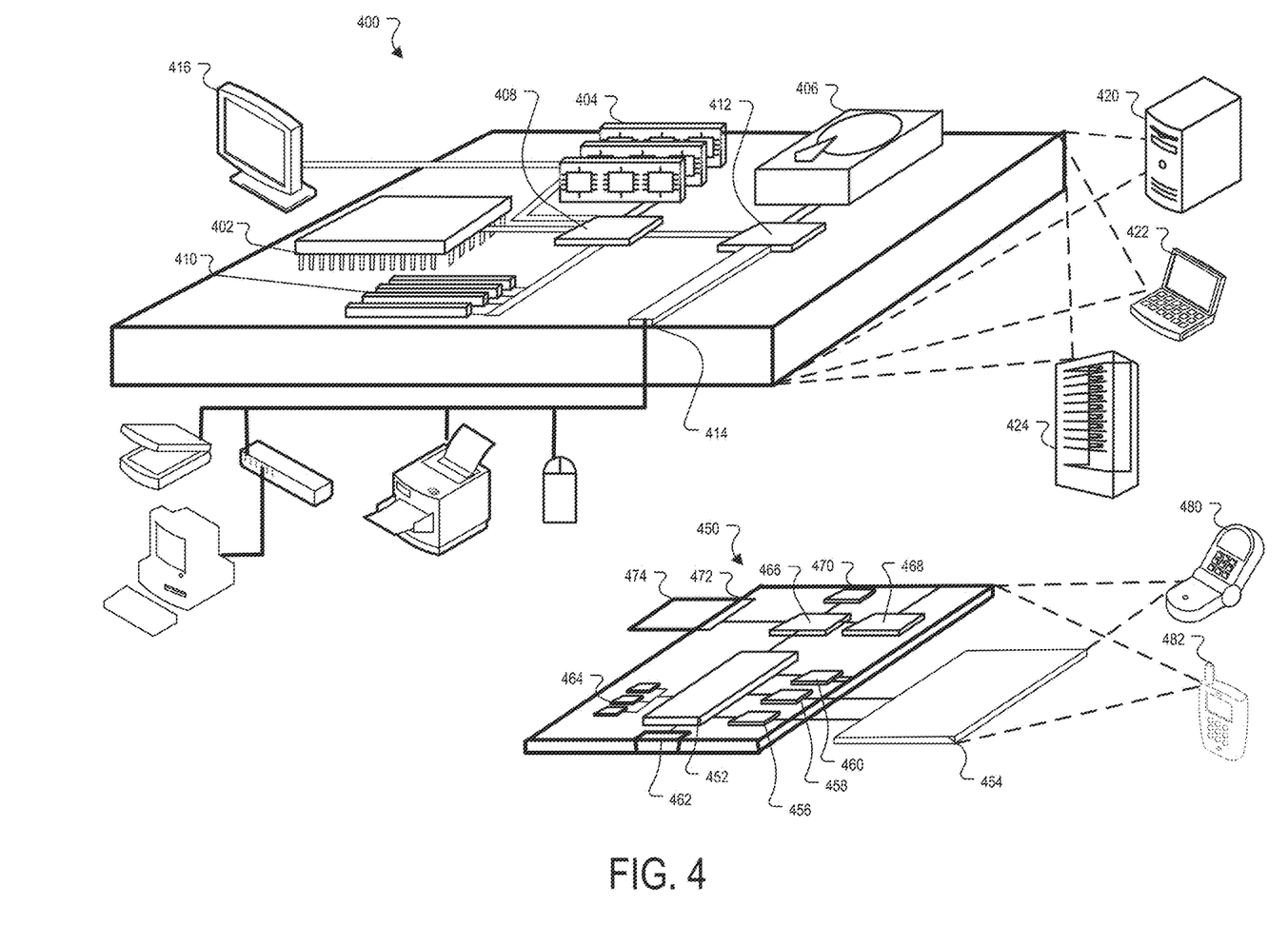
FIG. 4 shows an example of a computing device and a mobile computing device that can be used to implement the techniques described herein.

As described above, the Helmholtz device 202 of FIGS. 2 and 3 can be operated using software executed by a computing device (e.g., the computer system 212 of FIGS. 2 and 3). In some implementations, the software is included on a computer-readable medium for execution on the computer system 212. FIG. 4 shows an example computing device 400 and an example mobile computing device 450, which can be used to implement the techniques described herein. For example, calibration of the sensor 112 and/or calibration of the paired coils 220, 230, 240 of the Helmholtz device 202 may be executed and controlled by the computing device 400 and/or the mobile computing device 450. Computing device 400 is intended to represent various forms of digital computers, including, e.g., laptops, desktops, workstations, personal digital assistants, servers, blade servers, mainframes, and other appropriate computers. Computing device 450 is intended to represent various forms of mobile devices, including, e.g., personal digital assistants, cellular telephones, smartphones, and other similar computing devices. The components shown here, their connections and relationships, and their functions, are meant to be examples only, and are not meant to limit implementations of the techniques described and/or claimed in this document.

Computing device 400 includes processor 402, memory 404, storage device 406, high-speed interface 408 connecting to memory 404 and high-speed expansion ports 410, and low speed interface 412 connecting to low speed bus 414 and storage device 406. Each of components 402, 404, 406, 408, 410, and 412, are interconnected using various busses, and can be mounted on a common motherboard or in other manners as appropriate. Processor 402 can process instructions for execution within computing device 400, including instructions stored in memory 404 or on storage device 406, to display graphical data for a GUI on an external input/output device, including, e.g., display 416 coupled to high-speed interface 408. In some implementations, multiple processors and/or multiple buses can be used, as appropriate, along with multiple memories and types of memory. In addition, multiple computing devices 400 can be connected, with each device providing portions of the necessary operations (e.g., as a server bank, a group of blade servers, a multi-processor system, etc.).

Memory 404 stores data within computing device 400. In some implementations, memory 404 is a volatile memory unit or units. In some implementation, memory 604 is a non-volatile memory unit or units. Memory 404 also can be another form of computer-readable medium, including, e.g., a magnetic or optical disk.

Storage device 406 is capable of providing mass storage for computing device 400. In some implementations, storage device 406 can be or contain a computer-readable medium, including, e.g., a floppy disk device, a hard disk device, an optical disk device, a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 404, storage device 406, memory on processor 402, and the like.

High-speed controller 408 manages bandwidth-intensive operations for computing device 400, while low speed controller 412 manages lower bandwidth-intensive operations. Such allocation of functions is an example only. In some implementations, high-speed controller 408 is coupled to memory 404, display 416 (e.g., through a graphics processor or accelerator), and to high-speed expansion ports 410, which can accept various expansion cards (not shown). In some implementations, the low-speed controller 412 is coupled to storage device 406 and low-speed expansion port 414. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router (e.g., through a network adapter).

Computing device 400 can be implemented in a number of different forms, as shown in FIG. 4. For example, the computing device 400 can be implemented as standard server 420, or multiple times in a group of such servers. The computing device 400 can also can be implemented as part of rack server system 424. In addition or as an alternative, the computing device 400 can be implemented in a personal computer (e.g., laptop computer 422). In some examples, components from computing device 400 can be combined with other components in a mobile device (e.g., the mobile computing device 450). Each of such devices can contain one or more of computing device 400, 450, and an entire system can be made up of multiple computing devices 400, 450 communicating with each other.

Computing device 450 includes processor 452, memory 464, and an input/output device including, e.g., display 454, communication interface 466, and transceiver 468, among other components. Device 450 also can be provided with a storage device, including, e.g., a microdrive or other device, to provide additional storage. Components 450, 452, 464, 454, 466, and 468, may each be interconnected using various buses, and several of the components can be mounted on a common motherboard or in other manners as appropriate.

Processor 452 can execute instructions within computing device 450, including instructions stored in memory 464. The processor 452 can be implemented as a chipset of chips that include separate and multiple analog and digital processors. The processor 452 can provide, for example, for the coordination of the other components of device 450, including, e.g., control of user interfaces, applications run by device 450, and wireless communication by device 450.

Processor 452 can communicate with a user through control interface 458 and display interface 456 coupled to display 454. Display 454 can be, for example, a TFT LCD (Thin-Film-Transistor Liquid Crystal Display) or an OLED (Organic Light Emitting Diode) display, or other appropriate display technology. Display interface 456 can comprise appropriate circuitry for driving display 454 to present graphical and other data to a user. Control interface 458 can receive commands from a user and convert them for submission to processor 452. In addition, external interface 462 can communicate with processor 442, so as to enable near area communication of device 450 with other devices. External interface 462 can provide, for example, for wired communication in some implementations, or for wireless communication in some implementations. Multiple interfaces also can be used.

Memory 464 stores data within computing device 450. Memory 464 can be implemented as one or more of a computer-readable medium or media, a volatile memory unit or units, or a non-volatile memory unit or units. Expansion memory 474 also can be provided and connected to device 450 through expansion interface 472, which can include, for example, a SIMM (Single In Line Memory Module) card interface. Such expansion memory 474 can provide extra storage space for device 450, and/or may store applications or other data for device 450. Specifically, expansion memory 474 can also include instructions to carry out or supplement the processes described above and can include secure data. Thus, for example, expansion memory 474 can be provided as a security module for device 450 and can be programmed with instructions that permit secure use of device 450. In addition, secure applications can be provided through the SIMM cards, along with additional data, including, e.g., placing identifying data on the SIMM card in a non-hackable manner.

The memory 464 can include, for example, flash memory and/or NVRAM memory, as discussed below. In some implementations, a computer program product is tangibly embodied in a data carrier. The computer program product contains instructions that, when executed, perform one or more methods, including, e.g., those described above with respect to calibrating the sensor 112 and/or calibrating the paired coils 220, 230, 240 of the Helmholtz device 202. The data carrier is a computer- or machine-readable medium, including, e.g., memory 464, expansion memory 474, and/or memory on processor 452, which can be received, for example, over transceiver 468 or external interface 462.

Device 450 can communicate wirelessly through communication interface 466, which can include digital signal processing circuitry where necessary. Communication interface 466 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 468. In addition, short-range communication can occur, including, e.g., using a Bluetooth®, WiFi, or other such transceiver (not shown). In addition, GPS (Global Positioning System) receiver module 470 can provide additional navigation- and location-related wireless data to device 450, which can be used as appropriate by applications running on device 450.

Device 450 also can communicate audibly using audio codec 460, which can receive spoken data from a user and convert it to usable digital data. Audio codec 460 can likewise generate audible sound for a user, including, e.g., through a speaker, e.g., in a handset of device 450. Such sound can include sound from voice telephone calls, recorded sound (e.g., voice messages, music files, and the like) and also sound generated by applications operating on device 450.

Computing device 450 can be implemented in a number of different forms, as shown in FIG. 4. For example, the computing device 450 can be implemented as cellular telephone 480. The computing device 450 also can be implemented as part of smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system. This includes at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described herein can be implemented on a computer having a display device (e.g., a CRT (cathode ray tube) or LCD (liquid crystal display) monitor) for presenting data to the user, and a keyboard and a pointing device (e.g., a mouse or a trackball) by which the user can provide input to the computer. Other kinds of devices can be used to provide for interaction with a user as well. For example, feedback provided to the user can be a form of sensory feedback (e.g., visual feedback, auditory feedback, or tactile feedback). Input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such backend, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the components described herein can be separated, combined or incorporated into a single or combined component. The components depicted in the figures are not intended to limit the systems described herein to the software architectures shown in the figures.

A number of embodiments have been described. Nevertheless, it will be understood that various modifications may be made without departing from the spirit and scope of the disclosure. Accordingly, other embodiments are within the scope of the following claims.

What is claimed is:

1. A calibration system comprising:
a Helmholtz device comprising three pairs of coils defining an inner volume, wherein each of the three pairs of coils is configured to generate a magnetic field that is uniform throughout the inner volume; and
a computer system configured to communicate with the Helmholtz device and a first magnetic sensor of a device, wherein at least a portion of the device is positioned within the inner volume such that the first magnetic sensor is positioned at or near a center of the inner volume,
wherein the computer system is configured to:

provide instructions to cause each of the three pairs of coils to generate a first magnetic field;

receive signals from the first magnetic sensor that are based on characteristics of the first magnetic fields received at the first magnetic sensor;

measure, based on the signals received from the first magnetic sensor, one or more characteristics of the first magnetic sensor; and determine, using a calibration algorithm, one or more calibration correction factors for the first magnetic sensor based on the one or more characteristics of the first magnetic sensor and the provided instructions, wherein a reference device that includes a second magnetic sensor is configured to be positioned within the inner volume such that the second magnetic sensor is positioned at or near a center of the inner volume, and wherein the computer system is further configured to:

provide instructions to cause each of the three pairs of coils to generate a second magnetic field that is uniform throughout the inner volume;

receive signals from the second magnetic sensor that are based on characteristics of the second magnetic fields received at the second magnetic sensor;

measure, based on the signals received from the second magnetic sensor, one or more characteristics of the second magnetic sensor; and determine, using a calibration algorithm, one or more calibration correction factors for one or more of the three pairs of coils based on the one or more characteristics of the second magnetic sensor.

2. The calibration system of claim 1, wherein the computer system is further configured to:

create a calibration file that includes the calibration correction factors for the first magnetic sensor; and apply the calibration file to the first magnetic sensor.

3. The calibration system of claim 1, wherein the device is a head-mounted display, and a mount is configured to hold the head-mounted display and the first magnetic sensor in a fixed position and orientation relative to the Helmholtz device.

4. The calibration system of claim 1, wherein the device is a head-mounted display configured to communicate with one or both of the computer system or the Helmholtz device.

5. The calibration system of claim 1, wherein the device is a head-mounted display configured for use in one of both of an Augmented Reality (AR) system or a Virtual Reality (VR) system.

6. The calibration system of claim 1, wherein each of the three pairs of coils is configured to generate the magnetic field at a frequency of less than 100 Hz.

7. The calibration system of claim 6, wherein each of the three pairs of coils is configured to generate the magnetic field at a frequency of 90 Hz.

8. The calibration system of claim 7, wherein the first magnetic sensor is configured to receive magnetics fields having frequencies of more than 30 KHz when in use in an AR system or a VR system.

9. The calibration system of claim 1, wherein the second magnetic sensor is a calibrated magnetic sensor.

10. The calibration system of claim 1, wherein the computer system is further configured to:

create one or more calibration files that include the calibration correction factors for the one or more of the three pairs of coils; and apply the one or more calibration files to the one or more of the three pairs of coils.

11. The calibration system of claim 1, wherein the instructions for causing each of the three pairs of coils to generate the magnetic field are adjusted based on the one or more calibration correction factors for the one of more of the three pairs of coils.

12. The calibration system of claim 1, wherein measuring, based on the signals received from the first magnetic sensor, one or more characteristics of the first magnetic sensor comprises measuring the position and orientation of the first magnetic sensor.

13. The calibration system of claim 12, wherein the one or more calibration correction factors for the first magnetic sensor are based at least in part on the measured position and orientation of the first magnetic sensor.

14. A method comprising:

providing, by a computer system, instructions to cause current to flow through each of three pairs of coils that define an inner volume, wherein the current causes each of the three pairs of coils to generate a first magnetic field that is uniform throughout the inner volume;

receiving, from a first magnetic sensor incorporated into a device that is positioned within the inner volume, signals that are based on characteristics of the first magnetic fields received at the first magnetic sensor;

measuring, based on the signals received from the first magnetic sensor, one or more characteristics of the first magnetic sensor; and determining, using a calibration algorithm, one or more calibration correction factors for the first magnetic sensor based on the one or more characteristics of the first magnetic sensor and the provided instructions, wherein a reference device that includes a second magnetic sensor is configured to be positioned within the inner volume such that the second magnetic sensor is positioned at or near a center of the inner volume, and wherein the method further comprises:

providing, by the computer system, instructions to cause second current to flow through each of the three pairs of coils, wherein the second current causes each of the three pairs of coils to generate a second magnetic field that is uniform throughout the inner volume;

receiving signals from the second magnetic sensor that are based on characteristics of the second magnetic fields received at the second magnetic sensor;

measuring, based on the signals received from the second magnetic sensor, one or more characteristics of the second magnetic sensor; and determining, using a calibration algorithm, one or more calibration correction factors for one or more of the three pairs of coils based on the one or more characteristics of the second magnetic sensor.

15. The method of claim 14, further comprising:

creating a calibration file that includes the calibration correction factors for the first magnetic sensor; and applying the calibration file to the first magnetic sensor.

16. The method of claim 14, wherein the device is a head-mounted display, and a mount is configured to hold the head-mounted display and the first magnetic sensor in a fixed position and orientation relative to the three pairs of coils.

17. The method of claim 14, wherein one or more of the first magnetic sensor, the device, or the three pairs of coils are configured to communicate with the computer system.

18. The method of claim 14, wherein the device is a head-mounted display configured for use in one of both of an Augmented Reality (AR) system or a Virtual Reality (VR) system.

19. The method of claim 14, wherein each of the three pairs of coils is configured to generate the magnetic field at a frequency of less than 100 Hz.

20. The method of claim 19, wherein each of the three pairs of coils is configured to generate the magnetic field at a frequency of 90 Hz.

21. The method of claim 20, wherein the first magnetic sensor is configured to receive magnetics fields having frequencies of more than 30 KHz when in use in an AR system or a VR system.

22. The method of claim 14, further comprising:
- creating one or more calibration files that include the calibration correction factors for the one or more of the three pairs of coils; and
- applying the one or more calibration files to the one or more of the three pairs of coils.

23. The method of claim 14, wherein the instructions for causing each of the three pairs of coils to generate the magnetic field are adjusted based on the one or more calibration correction factors for the one of more of the three pairs of coils.

* * * * *